(12) United States Patent
Ambrosio

(10) Patent No.: US 9,456,860 B2
(45) Date of Patent: Oct. 4, 2016

(54) BIORESORBABLE FOAMING TISSUE DRESSING

(75) Inventor: Archel Ambrosio, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 781 days.

(21) Appl. No.: 12/347,791

(22) Filed: Dec. 31, 2008

(65) Prior Publication Data

US 2009/0157017 A1  Jun. 18, 2009

Related U.S. Application Data

(63) Continuation-in-part of application No. 11/724,073, filed on Mar. 13, 2007, now Pat. No. 8,267,918.

(60) Provisional application No. 60/782,171, filed on Mar. 14, 2006.

(51) Int. Cl.

| | |
|---|---|
| A61K 47/36 | (2006.01) |
| A61K 38/18 | (2006.01) |
| A61M 1/00 | (2006.01) |
| A61K 47/02 | (2006.01) |
| A61K 35/12 | (2015.01) |
| A61K 47/42 | (2006.01) |
| A61K 47/32 | (2006.01) |
| A61B 17/88 | (2006.01) |
| A61F 13/00 | (2006.01) |
| A61L 15/20 | (2006.01) |
| A61L 15/42 | (2006.01) |
| A61L 15/54 | (2006.01) |
| A61L 15/60 | (2006.01) |
| A61L 15/64 | (2006.01) |
| A61L 26/00 | (2006.01) |
| A61F 13/40 | (2006.01) |
| A61M 37/00 | (2006.01) |
| A61B 17/80 | (2006.01) |
| A61F 2/30 | (2006.01) |
| A61F 2/36 | (2006.01) |

(52) U.S. Cl.
CPC ............. *A61B 17/88* (2013.01); *A61F 2/3662* (2013.01); *A61F 13/00017* (2013.01); *A61F 13/00063* (2013.01); *A61F 13/00068* (2013.01); *A61L 15/20* (2013.01); *A61L 15/425* (2013.01); *A61L 15/54* (2013.01); *A61L 15/60* (2013.01); *A61L 15/64* (2013.01); *A61L 26/008* (2013.01); *A61L 26/009* (2013.01); *A61L 26/0066* (2013.01); *A61L 26/0085* (2013.01); *A61M 1/0088* (2013.01); *A61M 35/006* (2013.01); *A61M 37/00* (2013.01); *A61B 17/80* (2013.01); *A61F 2/30767* (2013.01); *A61F 2/36* (2013.01); *A61F 2002/30677* (2013.01); *A61F 2002/30785* (2013.01); *A61F 2002/30787* (2013.01); *A61F 2002/30968* (2013.01); *A61F 2002/368* (2013.01); *A61F 2002/3611* (2013.01); *A61F 2002/3625* (2013.01); *A61F 2002/3694* (2013.01); *A61F 2013/0054* (2013.01); *A61F 2013/0074* (2013.01); *A61F 2013/00157* (2013.01); *A61F 2013/00174* (2013.01); *A61F 2013/00221* (2013.01); *A61F 2013/00255* (2013.01); *A61F 2013/00519* (2013.01); *A61F 2013/00863* (2013.01); *A61F 2013/00927* (2013.01); *A61F 2310/00395* (2013.01); *A61F 2310/00592* (2013.01); *A61F 2310/00928* (2013.01); *A61L 2300/406* (2013.01); *A61L 2300/414* (2013.01); *A61L 2300/64* (2013.01)

(58) Field of Classification Search
None
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,382,867 | A | 5/1968 | Reaves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

Ma et al. "A preliminary in vitro study on the fabrication and tissue engineering applications of a novel chitosan bilayer material as a scaffold of human neofetal dermal fibroblasts" Biomaterials, 22, 2001, pp. 311-336.*

(Continued)

*Primary Examiner* — Bethany Barham
*Assistant Examiner* — Melissa Javier

(57) ABSTRACT

Provided is a flowable bioresorbable tissue dressing comprising a gas-forming porogen and a gel or gel-forming solution. Also provided is kits for preparing the above-described tissue dressing. Further provided are methods of treating a tissue site of a mammal with the above dressing. Also provided is a reduced pressure delivery system for applying a reduced pressure tissue treatment to a tissue site.

43 Claims, No Drawings

(56) References Cited

U.S. PATENT DOCUMENTS

| | | | |
|---|---|---|---|
| 3,826,254 A | 7/1974 | Mellor | |
| 3,867,319 A | 2/1975 | Lundberg | |
| 3,993,080 A | 11/1976 | Loseff | |
| 4,029,104 A | 6/1977 | Kerber | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,324,262 A | 4/1982 | Hall | |
| 4,329,743 A | 5/1982 | Alexander et al. | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,479,792 A | 10/1984 | Lazarus et al. | |
| 4,480,638 A | 11/1984 | Schmid | |
| 4,523,920 A | 6/1985 | Russo | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,572,906 A | 2/1986 | Sparkes et al. | |
| 4,579,555 A | 4/1986 | Russo | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,681,570 A | 7/1987 | Dalton | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,830,856 A | 5/1989 | Peppers | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,936,834 A | 6/1990 | Beck et al. | |
| 4,941,882 A | 7/1990 | Ward et al. | |
| 4,948,575 A | 8/1990 | Cole et al. | |
| 4,953,565 A | 9/1990 | Tachibana et al. | |
| 4,969,880 A | 11/1990 | Zamierowski | |
| 4,985,019 A | 1/1991 | Michelson | |
| 5,034,006 A | 7/1991 | Hosoda et al. | |
| 5,037,397 A | 8/1991 | Kalt et al. | |
| 5,045,056 A | 9/1991 | Behl | |
| 5,057,606 A | 10/1991 | Garbe | |
| 5,086,170 A | 2/1992 | Luheshi et al. | |
| 5,089,606 A * | 2/1992 | Cole et al. .............. | 536/54 |
| 5,092,858 A | 3/1992 | Benson et al. | |
| 5,100,395 A | 3/1992 | Rosenberg | |
| 5,100,396 A | 3/1992 | Zamierowski | |
| 5,108,364 A | 4/1992 | Takezawa et al. | |
| 5,116,310 A | 5/1992 | Seder et al. | |
| 5,134,994 A | 8/1992 | Say | |
| 5,149,331 A | 9/1992 | Ferdman et al. | |
| 5,163,905 A | 11/1992 | Don Michael | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,254,084 A | 10/1993 | Geary | |
| 5,259,399 A | 11/1993 | Brown | |
| 5,261,893 A | 11/1993 | Zamierowski | |
| 5,266,071 A | 11/1993 | Elftman | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,324,306 A | 6/1994 | Makower et al. | |
| 5,342,376 A | 8/1994 | Ruff | |
| 5,344,415 A | 9/1994 | DeBusk et al. | |
| 5,358,494 A | 10/1994 | Svedman | |
| 5,376,376 A | 12/1994 | Li | |
| 5,405,322 A | 4/1995 | Lennox et al. | |
| 5,437,622 A | 8/1995 | Carion | |
| 5,437,651 A | 8/1995 | Todd et al. | |
| 5,443,481 A | 8/1995 | Lee | |
| 5,527,293 A | 6/1996 | Zamierowski | |
| 5,549,579 A | 8/1996 | Batdorf et al. | |
| 5,549,584 A | 8/1996 | Gross | |
| 5,556,375 A | 9/1996 | Ewall | |
| 5,569,184 A | 10/1996 | Crocker et al. | |
| 5,591,183 A | 1/1997 | Chin | |
| 5,607,388 A | 3/1997 | Ewall | |
| 5,634,935 A | 6/1997 | Taheri | |
| 5,636,643 A | 6/1997 | Argenta et al. | |
| 5,645,081 A | 7/1997 | Argenta et al. | |
| 5,676,634 A | 10/1997 | Khouri | |
| 5,681,342 A | 10/1997 | Benchetrit | |
| 5,738,656 A | 4/1998 | Wagner | |
| 5,820,581 A | 10/1998 | Wolfinbarger, Jr. | |
| 5,885,508 A | 3/1999 | Ishida | |
| 5,888,544 A | 3/1999 | Gergely et al. | |
| 5,914,264 A | 6/1999 | Korman | |
| 5,948,020 A | 9/1999 | Yoon et al. | |
| RE36,370 E | 11/1999 | Li | |
| 5,980,503 A | 11/1999 | Chin | |
| 5,984,942 A | 11/1999 | Alden et al. | |
| 6,013,054 A | 1/2000 | Jium Yan | |
| 6,042,537 A | 3/2000 | Kaiser | |
| 6,071,267 A | 6/2000 | Zamierowski | |
| 6,086,587 A | 7/2000 | Hawk | |
| 6,132,415 A | 10/2000 | Finch et al. | |
| 6,135,116 A | 10/2000 | Vogel et al. | |
| 6,142,982 A | 11/2000 | Hunt et al. | |
| 6,153,292 A * | 11/2000 | Bell et al. ................ | 428/305.5 |
| 6,174,306 B1 | 1/2001 | Fleischmann | |
| 6,241,747 B1 | 6/2001 | Ruff | |
| 6,285,903 B1 | 9/2001 | Rosenthal et al. | |
| 6,287,316 B1 | 9/2001 | Agarwal et al. | |
| 6,345,623 B1 | 2/2002 | Heaton et al. | |
| 6,394,948 B1 | 5/2002 | Borst et al. | |
| 6,398,767 B1 | 6/2002 | Fleischmann | |
| 6,458,109 B1 | 10/2002 | Henley et al. | |
| 6,478,960 B1 | 11/2002 | Saruhashi et al. | |
| 6,488,643 B1 | 12/2002 | Tumey et al. | |
| 6,493,568 B1 | 12/2002 | Bell et al. | |
| 6,500,112 B1 | 12/2002 | Khouri | |
| 6,511,650 B1 | 1/2003 | Eiselt et al. | |
| 6,528,097 B1 * | 3/2003 | Vaughn et al. .............. | 424/501 |
| 6,551,280 B1 | 4/2003 | Knighton et al. | |
| 6,553,998 B2 | 4/2003 | Heaton et al. | |
| 6,613,026 B1 | 9/2003 | Palasis et al. | |
| 6,641,575 B1 | 11/2003 | Lonky | |
| 6,685,681 B2 | 2/2004 | Lockwood et al. | |
| 6,695,823 B1 | 2/2004 | Lina et al. | |
| 6,752,794 B2 | 6/2004 | Lockwood et al. | |
| 6,755,796 B2 | 6/2004 | Spector | |
| 6,755,807 B2 | 6/2004 | Risk, Jr. et al. | |
| 6,758,836 B2 | 7/2004 | Zawacki | |
| 6,764,497 B2 | 7/2004 | Fogarty et al. | |

(56) References Cited

U.S. PATENT DOCUMENTS

| | | | |
|---|---|---|---|
| 6,800,074 | B2 | 10/2004 | Henley et al. |
| 6,814,079 | B2 | 11/2004 | Heaton et al. |
| 6,824,533 | B2 | 11/2004 | Risk, Jr. et al. |
| 6,840,960 | B2 | 1/2005 | Bubb |
| 6,855,135 | B2 | 2/2005 | Lockwood et al. |
| 6,866,805 | B2 | 3/2005 | Hong et al. |
| 6,871,740 | B1 | 3/2005 | Cao |
| 6,979,324 | B2 | 12/2005 | Bybordi et al. |
| 7,322,971 | B2 | 1/2008 | Shehada |
| 7,753,902 | B1 | 7/2010 | Mansour et al. |
| 7,935,363 | B2* | 5/2011 | Ratcliffe ............ 424/443 |
| 7,976,533 | B2 | 7/2011 | Larsson |
| 7,981,098 | B2 | 7/2011 | Boehringer et al. |
| 2002/0028243 | A1 | 3/2002 | Masters |
| 2002/0077661 | A1 | 6/2002 | Saadat |
| 2002/0111576 | A1* | 8/2002 | Greene et al. ............ 602/42 |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0161346 | A1 | 10/2002 | Lockwood et al. |
| 2002/0198503 | A1 | 12/2002 | Risk, Jr. et al. |
| 2003/0009187 | A1 | 1/2003 | Fogarty et al. |
| 2003/0014022 | A1 | 1/2003 | Lockwood et al. |
| 2003/0021832 | A1 | 1/2003 | Scherr |
| 2003/0033017 | A1 | 2/2003 | Lotz et al. |
| 2003/0057070 | A1 | 3/2003 | Wang et al. |
| 2003/0088209 | A1 | 5/2003 | Chiu et al. |
| 2003/0167031 | A1 | 9/2003 | Odland |
| 2003/0216672 | A1 | 11/2003 | Rastegar et al. |
| 2004/0006319 | A1 | 1/2004 | Lina et al. |
| 2004/0039391 | A1 | 2/2004 | Argenta et al. |
| 2004/0064111 | A1 | 4/2004 | Lockwood et al. |
| 2004/0071949 | A1 | 4/2004 | Glatkowski et al. |
| 2004/0093026 | A1 | 5/2004 | Weidenhagen et al. |
| 2004/0093080 | A1 | 5/2004 | Helmus et al. |
| 2004/0098017 | A1 | 5/2004 | Saab et al. |
| 2004/0122434 | A1 | 6/2004 | Argenta et al. |
| 2004/0127862 | A1 | 7/2004 | Bubb et al. |
| 2004/0166088 | A1* | 8/2004 | Shalaby ............ 424/78.29 |
| 2004/0243167 | A1 | 12/2004 | Tanaka et al. |
| 2005/0065484 | A1 | 3/2005 | Watson, Jr. |
| 2005/0119617 | A1 | 6/2005 | Stecker et al. |
| 2005/0131327 | A1 | 6/2005 | Lockwood et al. |
| 2005/0192532 | A1 | 9/2005 | Kucklick et al. |
| 2005/0267577 | A1 | 12/2005 | Trieu |
| 2006/0024266 | A1 | 2/2006 | Brandom et al. |
| 2006/0142685 | A1 | 6/2006 | Addison et al. |
| 2006/0200003 | A1 | 9/2006 | Youssef |
| 2007/0156251 | A1 | 7/2007 | Karmon |
| 2007/0237811 | A1 | 10/2007 | Scherr |
| 2008/0033333 | A1 | 2/2008 | Macphee et al. |
| 2008/0114277 | A1 | 5/2008 | Ambrosio et al. |
| 2008/0206308 | A1 | 8/2008 | Jabbari et al. |
| 2008/0275409 | A1 | 11/2008 | Kane et al. |
| 2008/0319268 | A1 | 12/2008 | Michaeli et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0 300 621 A1 | 1/1989 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| GB | 2357765 B | 4/2004 |
| JP | S58-95841 U | 6/1983 |
| JP | 4129536 | 4/1992 |
| JP | 6-70746 U | 10/1994 |
| JP | H11-501837 | 2/1999 |
| JP | 2005-528167 | 9/2005 |
| KR | 10-2002-0000580 A | 1/2002 |
| SG | 71559 | 4/2002 |
| TW | 512066 | 12/2002 |
| TW | 558444 | 10/2003 |
| TW | 200612877 | 5/2006 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 96/30073 A1 | 10/1996 |
| WO | WO 97/18007 | 5/1997 |
| WO | WO 99/13793 | 3/1999 |
| WO | 03/057307 A1 | 7/2003 |
| WO | WO 03/057070 | 7/2003 |
| WO | 03/086232 A2 | 10/2003 |
| WO | WO 2004/071949 A2 | 8/2004 |
| WO | 2004073697 A1 | 9/2004 |
| WO | WO 2005/020849 A2 | 3/2005 |
| WO | WO 2005/105180 | 11/2005 |
| WO | 2006/014917 A2 | 2/2006 |
| WO | 2006/046060 A2 | 5/2006 |
| WO | 2008057600 A2 | 5/2008 |
| WO | 2008060475 A2 | 5/2008 |
| WO | 2008060622 A2 | 5/2008 |
| WO | 2008129318 A2 | 10/2008 |

OTHER PUBLICATIONS

Borzacchiello et al. "Chitosan based hydrogels: Synthesis and characterization" Journal of Materials Science: Materials in Medicine, 12, 2011, pp. 861-864.*

Lee et al. "Hydrogels for Tissue Engineering" Chemical Reviews, 101(7), 2001, pp. 1869-1879.*

Ma et al. "A preliminary in vitro study on the fabrication and tissue engineering applications of a novel chitosan bilayer material as a scaffold of human neofetal dermal fibroblasts" Biomaterials, 22, 2001, pp. 331-336.*

Response to Restriction Requirement filed Aug. 19, 2009 in U.S. Appl. No. 11/717,892.

Non-Final Office Action date mailed Oct. 28, 2009 in U.S. Appl. No. 11/717,892.

Examiner Interview Summary date mailed Dec. 30, 2009 in U.S. Appl. No. 11/717,892.

Response filed Jan. 25, 2010 to Non-Final Action date mailed Oct. 28, 2009 in U.S. Appl. No. 11/717,892.

Non-Final Office Action date mailed Oct. 1, 2009 in U.S. Appl. No. 11/717,854.

Examiner Interview Summary date mailed Dec. 11, 2009 in U.S. Appl. No. 11/717,854.

Response filed Dec. 23, 2009 to Non-Final Action dated Oct. 1, 2009 in U.S. Appl. No. 11/717,854.

Response filed Aug. 19, 2009 to Non-Final Action dated Jun. 18, 2009 in U.S. Appl. No. 11/807,834.

Final Office Action date mailed Oct. 2, 2009 in U.S. Appl. No. 11/807,834.

RCE/Amendment filed Jan. 27, 2010 in U.S. Appl. No. 11/807,834.

Non-Final Office Action date mailed Jan. 12, 2011 for U.S. Appl. No. 11/717,892.

Response filed Dec. 15, 2010 for U.S. Appl. No. 11/717,854.

Interview Summary date mailed Dec. 19, 2010 for U.S. Appl. No. 11/717,854.

Non-Final Office Action date mailed Jan. 21, 2011 for U.S. Appl. No. 11/724,073.

Non-Final Office Action date mailed Feb. 14, 2011 for U.S. Appl. No. 11/724,072.

Advisory Action date mailed Nov. 10, 2010 for U.S. Appl. No. 11/807,834.

(56) References Cited

OTHER PUBLICATIONS

RCE/Response filed Nov. 24, 2010 for U.S. Appl. No. 11/807,834.
Non-Final Office Action date mailed Feb. 18, 2011 for U.S. Appl. No. 11/807,834.
V.A.C.® Therapy Clinical Guidelines: A Reference Source for Clinicians (Jul. 2007).
Non-Final Rejection date mailed Mar. 18, 2010 in U.S. Appl. No. 11/717,854.
Non-Final Action date mailed Mar. 11, 2010 in U.S. Appl. No. 11/807,834.
Response filed Mar. 17, 2011 for U.S. Appl. No. 11/717,892.
Response filed Apr. 18, 2011 for U.S. Appl. No. 11/724,073.
Interview Summary date mailed Apr. 20, 2011 for U.S. Appl. No. 11/724,073.
Kilbride, et al. "Vacuum-assisted closure: a new method for treating patients with giant omphalocele", J Pediatr Surg; Jan. 2006; vol. 41, iss 1, pp. 212-215 (Abstract Only).
Davydov et al, "Vacuum-therapy of Wounds and Wound Process," Moscow, Meditsina, 1999, pp. 66-69 (English translation).
Express Abandonment filed Apr. 22, 2010 in U.S. Appl. No. 12/540,934.
Decision on Petition for Express Abandonment and Notice of Abandonment date mailed May 3, 2010 in U.S. Appl. No. 12/540,934.
Final Office Action date mailed May 16, 2011 for U.S. Appl. No. 11/717,854.
Interview Summary date mailed May 2, 2011 for U.S. Appl. No. 11/724,072.
Response filed May 12, 2011 for U.S. Appl. No. 11/724,072.
Response filed May 16, 2011 for U.S. Appl. No. 11/807,834.
Interview Summary date mailed May 17, 2011 for U.S. Appl. No. 11/807,834.
Notice of Allowance date mailed Jun. 2, 2011 for U.S. Appl. No. 11/717,892.
Kane et al "Controlled Induction of Distributed Microdeformation in Wounded Tissue via a Microchamber Array Dressing", pp. 333-340; Journal of Biomedical Materials Research; Nov. 2010, vol. 95A, Issue 2.
Non-Final Office Action date mailed Jun. 30, 2011 for U.S. Appl. No. 11/807,834.
Non-Final Office Action date mailed Jul. 27, 2010 for U.S. Appl. No. 11/717,892.
Interview Summary date mailed Jun. 11, 2010 for U.S. Appl. No. 11/807,834.
Response filed Jun. 14, 2010 for U.S. Appl. No. 11/807,834.
Response filed Jul. 1, 2010 for U.S. Appl. No. 11/717,854.
Interview Summary date mailed Jul. 6, 2010 for U.S. Appl. No. 11/717,854.
N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

(56) References Cited

OTHER PUBLICATIONS

M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
Marc G. Jeschke, MD, et al.; "Development of New Reconstructive Techniques: sue of Integra in Combination with Fibrin Glue and Negative-Pressure Therapy for Reconstruction of Acute and Chronic Wounds"; Plastic and Reconstructive Surgery, Feb. 2004, vol. 113, No. 2, pp. 525-530.
C. Daniel Medical, Inc.; All Silicone Jackson Pratt® Style Round Drain; www.cdanielmedical.com; Mar. 2007; 2 pgs.
C. Daniel Medical, Inc.; All Silicone Jackson Pratt® Style Flat Drain; www.cdanielmedical.com; Mar. 2007; 2 pgs.
Restriction Requirement date mailed Jul. 21, 2009 for U.S. Appl. No. 11/717,892.
Non-Final Office Action date mailed May 28, 2008 for U.S. Appl. No. 11/717,854.
Response filed Aug. 13, 2008 to Non-Final Office Action date mailed May 28, 2008 for U.S. Appl. No. 11/717,854.
Non-Final Office Action date mailed Nov. 13, 2008 for U.S. Appl. No. 11/717,854.
Response filed Dec. 12, 2008 to Non-Final Office Action date mailed Nov. 13, 2008 for U.S. Appl. No. 11/717,854.
Non-Final Office Action date mailed Mar. 5, 2009 for U.S. Appl. No. 11/717,854.
Response filed Jun. 25, 2009 to Non-Final Office Action date mailed Mar. 5, 2009 for U.S. Appl. No. 11/717,854.
Non-Final Office Action date mailed Jun. 18, 2009 for U.S. Appl. No. 11/807,834.
RCE/Response filed Aug. 10, 2011 for U.S. Appl. No. 11/717,854.
Interview Summary date mailed Aug. 11, 2011 for U.S. Appl. No. 11/717,854.
Non-Final Office Action date mailed Jul. 19, 2011 for U.S. Appl. No. 11/724,073.
Restriction Requirement date mailed Jul. 25, 2011 for U.S. Appl. No. 11/717,893.
Response filed Aug. 12, 2011 for U.S. Appl. No. 11/717,893.
Final Office Action date mailed Aug. 1, 2011 for U.S. Appl. No. 11/724,072.
Final Office Action date mailed Aug. 31, 2010 for U.S. Appl. No. 11/807,834.
International Search Report and Written Opinion date mailed Sep. 13, 2010 for PCT Application No. PCT/US2009/069495.
Non-Final Office Action date mailed Sep. 15, 2010 for U.S. Appl. No. 11/717,854.
RCE/Response filed Sep. 8, 2011 for U.S. Appl. No. 11/717,854.
Response filed Oct. 26, 2010 for U.S. Appl. No. 11/717,892.
Restriction Requirement date mailed Oct. 6, 2010 for U.S. Appl. No. 11/724,073.
Response filed Nov. 2, 2010 for U.S. Appl. No. 11/724,073.
Restriction Requirement date mailed Oct. 7, 2010 for U.S. Appl. No. 11/724,072.
Response filed Nov. 8, 2010 for U.S. Appl. No. 11/724,072.
Response filed Oct. 26, 2010 for U.S. Appl. No. 11/807,834.
Non-Final Office Action date mailed Oct. 4, 2011 for U.S. Appl. No. 11/717,893.
Express Abandonment filed Nov. 29, 2011 for U.S. Appl. No. 11/724,072.
Response filed Oct. 19, 2011 for U.S. Appl. No. 11/724,073.
Supplemental European Search Report issued on Jan. 22, 2013, in corresponding European Patent Application No. 07753292.7.
English translation of Official Action issued on Oct. 23, 2012, by the SIPO of China, in corresponding Chinese Patent Application No. 200980152490.4.
Supplementary European Search Report for corresponding EP Application 09837052.1, mailed Aug. 19, 2013.

\* cited by examiner

BIORESORBABLE FOAMING TISSUE DRESSING

CROSS-REFERENCE TO RELATED APPLICATIONS

This application is a continuation-in-part of prior application Ser. No. 11/724,073 filed Mar. 13, 2007 now U.S. Pat. No. 8,267,918, which claims the benefit of U.S. Provisional Application No. 60/782,171, filed Mar. 14, 2006, both of which are incorporated by reference.

BACKGROUND OF THE INVENTION

1. Field of the Invention

The present invention relates generally to tissue treatment systems and in particular to methods, systems and compositions for making and using a pourable and/or injectable gel or gel-forming solution.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including migration of epithelial tissue and subcutaneous tissue from the healthy tissue towards the tissue site, faster healing and increased formation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

Typically, the porous pad or other manifolding device is sized to fit the existing wound and placed in contact with the wound. The pad or device is then periodically replaced with smaller pieces of dressing as the wound begins to heal and becomes smaller. While use of reduced pressure therapy with the porous pad or other manifolding device has been highly successful, there still exist various difficulties with this process. For example, it may be difficult to obtain a porous pad or other manifolding device of a proper width, length or depth to adequately fill the wound. Further, as the porous pad or other manifolding device is removed it may also remove healthy tissue, thereby causing further trauma to the tissue site.

It has been previously proposed to use biodegradable materials to make the porous pad or other manifolding device, therefore negating the need to remove it from the tissue site. Further, other have attempted various methods to manufacturing biodegradable polymers in different shapes. In all of these methods, however, the biodegradable polymer is formed in advance into a particular shape. Individual wounds, however, are of inconsistent shapes and sizes.

Cavi-Care™ is a foam dressing produced by Smith & Nephew Healthcare Limited that is a two-part room temperature vulcanizing foam, where a polydiethylsiloxane base is mixed with a platinum catalyst and hydrogen gas-releasing agents, which react together to form that is poured onto a wound, where it conforms to the shape of the wound. Cavi-Care™ is not biodegradable and must be removed and cleansed on a regular basis. The foam Cavi-Care™ dressing is not porous enough to be used with reduced pressure therapy.

A need exists, therefore, for a bioabsorbable composition that conforms to the exact shape of a wound, where the composition may serve as a dressing. The present invention addresses that need.

SUMMARY

These and other needs are met through the use of a bioabsorbable tissue dressing designed to readily conform to the size and shape of the tissue site. Thus, in its broadest sense, the invention produces compositions, methods and systems for making and using gel or gel-forming solutions in various configurations.

A first embodiment in accordance with the invention is a flowable bioresorbable tissue dressing including a gas-forming porogen and a gel or gel-forming solution.

Another embodiment in accordance with the invention is a kit for preparing the above-described tissue dressing including a gas-forming porogen mixture in a first container and a gel or gel-forming solution or dehydrated ingredients for a gel or gel-forming solution in a second container.

Another embodiment in accordance with the invention is a method of treating a tissue site of a mammal with the above-described dressing including mixing the gas-forming porogen with the gel or gel-forming solution to create a flowable foaming mixture, then delivering the foaming mixture onto the tissue site while the mixture is foaming.

Another embodiment in accordance with the invention is a reduced pressure delivery system for applying a reduced pressure tissue treatment to a tissue site, including the above-described kit, a reduced pressure source, and a manifold. In these embodiments, the manifold comprises a reduced pressure delivery tube, where the reduced pressure tube comprises a proximal end, a distal end, and a lumen extending through the tube, where the proximal end is in fluid communication with the reduced pressure source and the distal end is in fluid communication with the dressing.

Other objects, features, and advantages of the present invention will become apparent with reference to the drawings and detailed description that follow.

DETAILED DESCRIPTION OF ILLUSTRATIVE EMBODIMENTS

These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

In the context of this specification, the term "reduced pressure" generally refers to a pressure that is less than the ambient pressure at a tissue site that is subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly greater than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure. Various methods and compositions describing reduced pressure treatment of tissue is described in the following patent publications: WO08091521A2, WO08042481A2, WO08036361A2, WO08036359A2, WO08036162A2, WO08013896A2, WO07143060A2, WO07133556A2, WO07133555A2, WO07106594A2, WO07106592A2, WO07106591A2, WO07106590A2, WO07106589A2, WO07092397A2, WO07067685A2, WO05033273A2, WO05009488A2, WO04105576A2, WO04060148A2, WO03092620A2, WO03018098A2, WO0061206A1, WO0038755A2, US20070123895, U.S. Pat. Nos. 7,351,250, 7,346,945, 7,316,672, 7,279,612, 7,214,202, 7,186,244, 7,108,683, 7,077,832, 7,070,584, 7,004,915, 6,994,702, 6,951,553, 6,936,037, 6,856,821, 6,814,079, 6,767,334, 6,695,823 and 6,135,116.

As used herein, the singular forms "a", "an" and "the" are intended to include the plural forms as well, unless the context clearly indicates otherwise. Additionally, the use of "or" is intended to include "and/or", unless the context clearly indicates otherwise.

The present application is based on the development of a tissue dressing that can be poured or injected into a tissue site, where the dressing has sufficient porosity such that it can be used as a scaffold through which reduced pressure treatment can be applied.

In some embodiments, the present application is directed to a flowable bioresorbable tissue dressing comprising a gas-forming porogen and a gel or gel-forming solution.

As used herein, a porogen is a dissolvable particle that is incorporated into a tissue engineering structure during the fabrication of the structure, and is then dissolved, leaving pores in the structure. A gas-forming porogen (also known as a gas foaming porogen) forms a gas such as carbon dioxide when dissolved, where the gas forms the pores in the structure by foaming.

These embodiments are not limited to any particular gas-forming porogen. In some embodiments, the porogen is a mixture of an acid and a salt, e.g., a carbonate salt. Carbon dioxide is formed upon the mixture of a carbonate salt and an acid. Examples of carbonate salts include ammonium bicarbonate, sodium bicarbonate and calcium carbonate. The use of calcium carbonate can result in a stronger foam than sodium bicarbonate since the $Ca^{+2}$ ions can form non-covalent crosslinks with commonly used anionic gels such as alginates or poloxamers. As is known in the art, poloxamers are nonionic amphoteric triblock copolymers that are also known as Pluronics®. See, e.g., U.S. Pat. No. 3,925, 241. A non-limiting example of a Pluronic® that is useful for the present invention is Pluronic® F127. Crosslinking stiffness can also be achieved by adding calcium sulfate hemihydrate to the dressing.

These embodiments are also not limited to any particular acid to mix with the salts. The skilled artisan could select an appropriate acid for any particular application without undue experimentation. In some embodiments, the acid is citric acid.

In these tissue dressings, the carbonate and acid may be used in stoichiometric amounts. It is also envisioned that the carbonate and acid are in some circumstances used in non-stoichiometric amounts.

In general, gels are apparently solid materials and have the structural cohesion of a solid. The gel can be either homogeneous or a heterogeneous mixture of more than one compound or structure. The gel-forming solution may be a liquid solution capable of forming a gel.

It will be readily apparent to one skilled in the art that the desired viscosity range may be achieved by varying the molecular weight and percent concentration of the materials in the formulation. For example, a gel having a low viscosity may be achieved by using low molecular weight materials or a low percentage concentration of materials, or a combination of the two. Conversely, a high viscosity gel may be achieved by using a higher molecular weight materials and a higher percent concentration. Intermediate viscosities may be achieved by varying the molecular weight and percent concentration accordingly.

The application is not limited to any particular chemical composition of the materials used for the gel or gel-forming solution. These compositions may include, but is not limited to, materials that form a gel spontaneously after hydration, materials that require cross-linking agents to form a gel, and the like. Further, the chemical composition of the gel may include water soluble polymers capable of forming a viscous aqueous solution or non-water soluble, water swellable polymers which can also form a viscous solution.

In some embodiments, the gel or gel-forming solution may be made of one or more bioresorbable materials, i.e., a biocompatible material whose degradation byproducts can be bioassimilated or excreted via natural pathways in the body, is dissolved in an appropriate solvent. In another embodiment, the gel or gel-forming solution includes one or more non-bioresorbable materials. In yet another embodiment, the gel or gel-forming solution includes both bioresorbable and non-bioresorbable materials.

The gel or gel-forming solution can also be thermoreversible, that is they can change from a liquid to a gel with an increase in temperature. Polymers composed of polyoxypropylene and polyoxyethylene are known to form thermoreversible gels when incorporated into aqueous solutions. These polymers have the ability to change from the liquid state to the gel state at temperatures close to body temperature. See, e.g., Roy, S. et al., 2001, Antimicrob Agents Chemother 45: 1671-1681.

Thus, the gel or gel-forming solution may include, but is not limited to, one or more of the following materials: vinyl polymers, polyoxyethylene-polyoxypropylene copolymers, polysaccharides, poly (ethylene oxide), polyethylene glycol, acrylamide polymers, synthetic and natural polyamino acids, glycolide polymers, poly(glycolic acid), poly(lactide-co-glycolide), polyurethanes, polyphosphazenes, poly(ethylene glycol)-poly(lactide-co-glycolide) co-polymer, polyhydroxyacids, ethylene glycol/lactide copolymers, polycarbonates, polyanhydrides, polyortho esters, polyacetals, degradable polycyanoacrylates, polycarbonates, polyfumarates, and derivatives or salts thereof. In one embodiment, the gel or gel-forming material includes polyoxyethylene-polyethylene glycol polymers.

The vinyl polymers may be one or more selected from the group of polyacrylic acid, polymethacrylic acid, polyvinyl pyrrolidone, lactide, poly(lactide), and polyvinyl alcohol.

Further, the materials of the gel or gel-forming solution may include one or more polysaccharides, for example cellulose or cellulose derivatives, glycosaminoglycans, agar, pectin, alginic acid, dextran, starch, or chitosan. It is contemplated that the starch may be in any form, including α-amylose and amylopectin. Suitable glycosaminoglycans include hyaluronic acid, chondroitin, chondroitin-4-sulfate, chondroitin-6-sulfate, dermatan sulfate, keratan sulfate, heparin sulfate and heparin.

The gel or gel-forming solution may also include one or more proteins, for example collagen, gelatin, albumin and fibronectin.

In addition, one or more of the materials of the gel or gel-forming solution may crosslink covalently or noncovalently to form the gel. This occurs, e.g., by use of a bifunctional reagent such as, for example, glutaraldehyde. Crosslinking can also be initiated by photopolymerization. For example, exposure of unsaturated groups including vinyl groups, allyl groups, cinnamates, acrylates, diacrylates, oligoacrylates, methacrylates, dimethacrylates, oligomethoacrylates, or other biologically acceptable photopolymerizable groups can result in cross-linking. Further, cross-linking can occur by temperature increases. For instance, materials which initiate free radical polymerization may crosslink at physiological temperatures. Such materials include, for example, potassium persulfate with or without tetramethyl ethylenediamine; benzoyl peroxide with or without triethanolamine; and ammonium persulfate with sodium bisulfite. Noncovalent crosslinking can occur between negatively charged and positively charged compounds. For example, negatively charged polyacrylate may be mixed with positively-charged chitosan resulting in crosslinking of the polymers and strengthening of the gel.

In some embodiments, the gel or gel-forming solution comprises Pluronic® F127, a polyacrylate, a poloxamer, a polyethylene glycol, chitosan, collagen, gelatin, hyaluronic acid, or combinations thereof. In specific embodiments, the gel or gel-forming solution comprises a combination of polyacrylate and chitosan.

The tissue dressing of these embodiments can further comprise a non-gas forming porogen, e.g., to add additional porosity to the dressing. Any compound known in the art as a porogen can potentially be used for these dressings, including salts, sugars, gelatin spheres or paraffin spheres. In some embodiments, the non-gas forming porogen is a salt. The application is not limited by the type of salt, as long as the salt is of an appropriate particle size and dissolvable in a fluid, i.e., a gas, liquid, or flowable material, including but not limited to, colloids, a liquid, a slurry, a suspension, a viscous gel, a paste, a putty, and particulate solids. Examples of appropriate salts used herein include, but are not limited to, sodium chloride and potassium chloride.

The non-gas forming porogen can also be a sugar, e.g., sucrose, saccharose, or any other sugar.

It is understood that the size of the resulting pores is dependent upon the type of porogen system used. For example, if the porogen system is a salt than the resulting pore size is approximately the size of the salt particles used. If, however, the porogen system is a gas-forming system, as with carbonate and acid, then the resulting pores size is dependent upon the size of the carbonate and acid particles and the amount of gas produced. As such, one may use any method to control the size of the porogen system, including but not limited to, sieving and centrifugation. In one embodiment, the porogen system is sieved through one or more screens to produce particles of a certain size. Thus, the pore size will be at a minimum the size of the particles produced by the sieving.

Further, the amount of porogen system used and the particle size of the porogen system will control the percent porosity of the resulting porous gel. It is understood that the percent porosity preferred by the practitioner may depend upon factors such as the mechanical properties of the materials used within the gel or gel-forming solution, such as bioresorbable polymers, the cell infiltration desired, the presence or absence of wound healing or tissue treatment substances, and the like. In one embodiment, the percent porosity is at least about 50%. In another embodiment, the percent porosity is about 70%.

Typically, the pore size produced by the porogen system(s) utilized herein is about 50 to about 1,500 microns. In one embodiment, the pore size is between about 100 and about 500 microns. In another embodiment, the pore size is between about 100 and about 250 microns.

In some embodiments, the tissue dressing further comprises a structure that adds mechanical strength to the dressing. Nonlimiting examples include a microsphere or a fiber or both.

Microspheres for incorporation into the dressing can be prepared by any means known in the art. For example, microspheres can be prepared by a spraying method, an an aqueous two phase method or an oil/water emulsion method, as they are known in the art. In the oil-in-water emulsion method the at least one bioresorbable polymer is dissolving in a solvent to form a first mixture. The polymer mixture is then added to an aqueous solution, preferably containing a surfactant, and vigorously agitated. The solvent is then evaporated off, leaving resulting microspheres. Pores in microspheres can be made using a gas-foaming porogen (Kim T K et al., 2006, Biomaterials 27:152-159).

The bioresorbable polymers for the microspheres can include, but are not limited to, lactide, poly(lactide) (PLA), glycolide polymers, poly(glycolic acid) (PGA), poly(lactide-co-glycolide) (PLGA), ethylene glycol/lactide copolymers, polycaprolactone (PCL), polyhydroxybutyrate, polyurethanes, polyphosphazenes, poly(ethylene glycol)-poly (lactide-co-glycolide) co-polymer, polyhydroxyacids, polycarbonates, polyamides, polyanhydrides, polyamino acids, polyortho esters, polyacetals, degradable polycyanoacrylates, polycarbonates, polyfumarates, degradable polyurethanes, proteins such as albumin, collagen, fibrin, synthetic and natural polyamino acids, polysaccharides such as alginate, heparin, and other naturally occurring biodegradable polymers of sugar units. In some embodiments, the structure comprises polylactide (PLA), polyglycolic acid (PLG), poly(lactide-co-glycolide) (PLGA), polyethylene glycol-PLA, PLA-polycaprolactone (PCL), a polyorthoester, a polyphosphazene, or a polyphosphoester. In more specific embodiments the microsphere comprises a PLA:PCL copolymer, where the ratio of PLA to PCL may range from 1000:1 to 1:100. In one embodiment, the PLA:PCL copolymer ratio is about 90:10. In another embodiment, the PLA:PCL copolymer ratio is about 80:20. In yet another embodiment, the PLA:PCL copolymer ratio is about 70:30.

Further, the size of the microspheres may be any size that is convenient to the practitioner. In one embodiment, the microsphere size is between about 50 to about 2,500 microns. In another embodiment, the microspheres are between about 100 and about 1,000 microns. In still another embodiment, the microspheres are between about 250 and about 500 microns. The size of the microspheres may be controlled by any means, including by not limited to, sieving and centrifugation. In one embodiment, the microspheres are sieved through one or more screens to produce microspheres of a certain size.

Staple fibers may also be incorporated into the tissue dressing for strength. The fibers can be made by any means known in the art. The fibers can also be made of any of the same ingredients as the microspheres described immediately above, including but not limited to polylactide (PLA), polyglycolic acid (PLG), poly(lactide-co-glycolide) (PLGA), polyethylene glycol-PLA, PLA-polycaprolactone (PCL), a polyorthoester, a polyphosphazene, or a polyphosphoester.

The fibers may be used in conjunction with any embodiment of this invention, and thus may be used with or without bioresorbable microspheres, various porogen systems, and the like for use with reduced pressure therapy systems.

In some embodiments, the dressing further comprises a bioactive agent, i.e., a compound or element (e.g., iron) that can improve the outcome of the treatment. Examples include nutritional supplements, antibiotics, small (<2000 mw) organic compounds (e.g., serotonin, prostaglandin, prostacyclin, thromboxane, histamine). peptides (e.g., bradykinin), nucleic acids (e.g., aptamers or genetic vectors), and proteins such as growth factors. These embodiments are not limited to the use of any particular growth factor. Examples of potentially useful growth factors within the scope of these embodiments include growth hormone (GH), a bone morphogenetic protein (BMP), transforming growth factor-α (TGF-α), a TGF-β, a fibroblast growth factor (FGF), granulocyte-colony stimulating factor (G-CSF), granulocyte/macrophage colony stimulating factor (GMCSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α) or nerve growth factor (NGF). The growth factor can be derived from any species, including human.

In some embodiments, the tissue dressing comprises a mammalian cell. Examples include an embryonic stem cell, an adult stem cell, an induced pluripotent stem cell, an epithelial cell, an endothelial cell, a mesenchymal cell, a muscle cell, a fibroblast, a chondrocyte, an adipocyte, or an osteocyte. The cell can be of any mammalian species, including humans.

Any of the above-described tissue dressings can be prepared in a kit form for ease of distribution and preparation. The present invention is thus also directed to a kit for preparing the above-described tissue dressing. The kit comprises a gas-forming porogen mixture in a first container and a gel or gel-forming solution or dehydrated ingredients for a gel or gel-forming solution in a second container. In some embodiments, the kit also comprises instructions for treating a tissue site with the dressing.

In various embodiments, the porogen is a mixture of an acid and a carbonate salt. The carbonate salt can be for example ammonium bicarbonate, sodium bicarbonate or calcium carbonate. These embodiments are also not limited to any particular acid to mix with the salts. In some embodiments, the acid is citric acid.

The application is not limited to any particular chemical composition of the materials used for the gel or gel-forming solution. In some embodiments, the gel or gel-forming solution comprises Pluronic® F127, a polyacrylate, a poloxamer, a polyethylene glycol, chitosan, collagen, gelatin, hyaluronic acid, or combinations thereof.

In various embodiments of these kits, the second container further comprises a structure that adds mechanical strength to the dressing. Nonlimiting examples of such structures include a microsphere or a fiber, as discussed above.

Some of these kits further comprise a bioactive agent, e.g., an antibiotic or growth factor. Other kits further comprise a mammalian cell, as discussed above.

The above-described tissue dressings can be used to treat tissue sites in a vertebrate, for example a mammal, including humans. Thus, in some embodiments, the invention is directed to a method of treating a tissue site of a mammal with the above-described tissue dressing. The method comprises mixing the gas-forming porogen with the gel or gel-forming solution to create a flowable foaming mixture, then delivering the foaming mixture onto the tissue site while the mixture is foaming.

The bioactive agents or cells utilized in the dressing may be combined at any time with the gel or gel-forming solution. Further, the bioactive agents may be covalently or non-covalently bound to the gel or gel-forming solution by, for example, use of a cross linker, inclusion of a specific reactive group, electrostatic interactions, hydrophilic interactions, hydrophobic interactions, attachment by use of molecules such as streptavidin, or through the use of a combination of covalent and non-covalent interactions.

The foaming mixture can be delivered onto the tissue site by any appropriate method. In some embodiments, the foaming mixture is delivered to the tissue site by pouring or injecting the mixture onto the tissue site. In other embodiments, the foaming mixture is delivered to the tissue site by delivery through a manifold delivery tube of a reduced pressure delivery system. The manifold delivery tube may be the same or different tube that reduced pressure is delivered from.

The foaming gel or gel-forming solution is thus poured, spread or injected into/onto the tissue site, where it forms a gel in situ at the tissue site. In one embodiment, the porogen system is allowed to completely react, i.e., the porogen system has stopped foaming and is incapable of forming additional pores, before placing the gel or gel-forming solution into the wound. In another embodiment, the gel or gel-forming solution is placed into/onto the wound while the porogen system is still foaming.

The resulting gel should be of sufficient increased mechanical strength that the gel and the pores formed by the porogen system will generally hold their shape in a reduced pressure environment, thus allowing flow of air and/or liquids through the pores. In some of these methods, the gas-forming porogen further comprises a structure that adds mechanical strength to the dressing. Examples of suitable structures include microspheres and staple fibers.

In various embodiments, the gel or gel-forming solution is thermoreversible. Such dressings are particularly useful when the dressing is injected or poured since the dressing will remain liquid until it is warmed at the tissue site.

These methods can be used on any vertebrate tissue site, such as on a mammal, including a human. In some embodiments, the tissue site comprises an exposed wound on the mammal. Examples of such wounds include an acute surgical wound, a pressure ulcer, a trauma wound, a diabetic wound, a skin graft, an open abdominal wound, or a burn.

The tissue site can also be a site of a defect such as a congenital defect or a defect due to the removal of tissue, e.g., due to cancer or infection. The present methods include utilization of the tissue dressing to encourage growth to fill such defects.

In some embodiments of these methods, the tissue site is an internal site and the foaming mixture is delivered to the tissue site percutaneously. Any internal site could be treated by these methods, including internal organs. In some embodiments, the tissue site is on a bone.

These tissue dressings can be utilized in reduced pressure treatment, provided the dressing comprises sufficient open pores that create a plurality of flow channels after the mixture stops foaming. In these embodiments, the method further comprises covering the dressing with a drape and applying a reduced pressure to the wound site through the dressing.

In some of these methods, reduced pressure is delivered to the wound site through a manifold. In these embodiments, the manifold comprises a reduced pressure delivery tube, wherein the reduced pressure tube comprises a proximal end, a distal end, and a lumen extending through the tube, and wherein the proximal end is in fluid communication with a reduced pressure source and the distal end is in fluid communication with the dressing.

In some embodiments of the methods utilizing reduced pressure, the tissue site and the gel are covered by a drape made of a flexible substance, in most cases made of impermeable materials, thus blocking or slowing the transmission of either liquids or gas. The drape will extend over the surface of the tissue site and gel and extend beyond the edges of the wound. At least one reduced pressure delivery tube is placed beneath the drape, and extends out from underneath the drape. The reduced pressure delivery tube is placed in fluid communication to a reduced pressure source, which preferably comprises a canister safely placed under the vacuum through fluid communication with a reduced pressure source.

Any structure and set up of the reduced pressure therapy device that is now known or later discovered could be utilized with these methods. In one embodiment, the tissue site and the gel are covered by a drape made of a flexible substance made preferably of impermeable materials, thus blocking or slowing the transmission of either liquids or gas. The drape will extend over the surface of the tissue site and gel and extend beyond the edges of the wound. At least one reduced pressure delivery tube is placed beneath the drape, and extends out from underneath the drape. The reduced pressure delivery tube is placed in fluid communication to a reduced pressure source.

Reduced pressure therapy is then applied to the wound. It is understood that the frequency and level of reduced pressure of the therapy treatment depends upon the location of the body, the size and shape of the tissue site, the composition of the gel, and the types of various ingredients applied to the site, if any. Further, depending upon the treatment regimen, reduced pressure therapy may be substantially continuous application or cyclical such that it oscillates the pressure over time.

In yet another embodiment, a manifold is placed over the gel dressing. The dressing and/or manifold facilitates substantially homogeneous reduced pressure distribution over the entire tissue site.

Reduced pressure therapy is then applied to the wound, compressing the gel and mechanically pressing the microspheres into the tissue site (305). The use of the microspheres is beneficial because the mechanical pressure against the wound promotes granulation, therefore reducing healing and/or tissue growth time.

In additional embodiments, the invention is directed to a reduced pressure delivery system for applying a reduced pressure tissue treatment to a tissue site. The system comprises the above identified kit for preparing the tissue dressing, a reduced pressure source, and a manifold. In these embodiments, the manifold comprises a reduced pressure delivery tube comprising a proximal end, a distal end, and a lumen extending through the tube. The proximal end of the tube is in fluid communication with the reduced pressure source and the distal end is in fluid communication with the dressing. In some of these embodiments, the manifold further comprises a second tube suitable for delivery of the above-described tissue dressing to a tissue site.

Preferred embodiments are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the example.

EXAMPLE 1

Production and Use of a Tissue Dressing Having a Gas-Forming Porogen in a Reduced Pressure Treatment System Prepare a pourable, in-situ foaming formulation comprising microspheres and a thermoreversible gel by first preparing 29% of Pluronic® F127 (BASF Corporation). The percent of Pluronic® F127 was selected because previous studies have indicated that 28% gelled slowly at 37° C. while 30% pluronic F127 gelled at room temperature overnight. Prepare 10 mL of 29% pluronic F1127 by dissolving 2.9 g of F127 in 10 mL $H_2O$. Place in refrigerator overnight to aid dissolution.

Combine 0.9 g calcium carbonate (Sigma, Incorporated) with 0.55 g citric acid (J.T. Baker) such that the resulting porogen system is in the amount of 50% of the F127 by dry weight. Prepare bioresorbable microspheres, and mix approximately 5 mL with the porogen system.

Add 200 µl $H_2O$ to the F127 solution and then add the F127 to the microsphere-porogen system mixture. Mix by hand, allowing the porogen system to react with the F127 solution. Transfer mixture to 37° C. water bath for 10 minutes.

Place in tissue site, connect to V.A.C.® therapy system, and seal with drape. Apply reduced pressure.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A dressing for applying reduced-pressure treatment to a tissue site, comprising:
   a gas-forming porogen comprising a particle size for developing sufficient porosity for conducting reduced pressure;
   a bioresorbable microsphere; and
   a bioresorbable gel or a bioresorbable gel-forming solution in a mixture with the gas-forming porogen and the bioresorbable microsphere;
   wherein the mixture is flowable, and after delivery to the tissue site, forms a scaffold comprising pores of at least 50 micrometers in diameter for delivering reduced pressure through the scaffold; and
   wherein the dressing is bioresorbable.

2. The dressing of claim 1, wherein the porogen is a mixture of an acid and a carbonate salt.

3. The dressing of claim 2, wherein the acid is citric acid.

4. The dressing of claim 2, wherein the carbonate salt is ammonium bicarbonate, sodium bicarbonate or calcium carbonate.

5. The dressing of claim 1, wherein the gel or gel-forming solution comprises collagen, gelatin, hyaluronic acid, or combinations thereof.

6. The dressing of claim 1, further comprising a non-gas forming porogen.

7. The dressing of claim 6, wherein the non-gas forming porogen is a salt.

8. The dressing of claim 7, wherein the salt is sodium chloride or potassium chloride.

9. The dressing of claim 6, wherein the non-gas forming porogen is a sugar.

10. The dressing of claim 1, wherein the bioresorbable microsphere comprises polylactide (PLA), polyglycolic acid (PLG), poly(lactide-co-glycolide) (PLGA), polyethylene glycol-PLA, PLA-polycaprolactone (PCL), a polyorthoester, a polyphosphazene, or a polyphosphoester.

11. The dressing of claim 1, further comprising a compound that adds stiffness to the dressing.

12. The dressing of claim 11, wherein the compound is calcium sulfate hemihydrate.

13. The dressing of claim 1, further comprising a bioactive agent.

14. The dressing of claim 13, wherein the bioactive agent is an antibiotic.

15. The dressing of claim 13, wherein the bioactive agent is a growth factor.

16. The dressing of claim 15, wherein the growth factor is growth hormone (GH), a bone morphogenetic protein (BMP), transforming growth factor-α(TGF-α), a TGF-β, a fibroblast growth factor (FGF), granulocyte-colony stimulating factor (G-CSF), granulocyte/macrophage colony stimulating factor (GMCSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α(TNF-α), or nerve growth factor (NGF).

17. The dressing of claim 1, further comprising a mammalian cell.

18. The dressing of claim 17, wherein the mammalian cell is an embryonic stem cell, an adult stem cell, an induced pluripotent stem cell, an epithelial cell, an endothelial cell, a mesenchymal cell, a muscle cell, a fibroblast, a chondrocyte, an adipocyte, or an osteocyte.

19. The dressing of claim 17, wherein the mammalian cell is a human cell.

20. The dressing of claim 1, wherein the pores of the scaffold are between approximately 50 micrometers and 1,500 micrometers in diameter.

21. The dressing of claim 1, wherein the pores of the scaffold are between approximately 100 micrometers and 500 micrometers in diameter.

22. A tissue dressing for applying reduced-pressure treatment to a tissue site, comprising:
 a gas-forming porogen comprising a particle size for developing sufficient porosity for conducting reduced pressure;
 a bioresorbable microsphere; and
 a gel or gel-forming solution in a mixture with the gas-forming porogen and the bioresorbable microsphere;
 wherein the mixture is flowable, and after delivery to the tissue site, forms a scaffold comprising pores of at least 50 micrometers in diameter for delivering reduced pressure through the scaffold.

23. The dressing of claim 22, wherein the porogen is a mixture of an acid and a carbonate salt.

24. The dressing of claim 23, wherein the acid is citric acid.

25. The dressing of claim 23, wherein the carbonate salt is ammonium bicarbonate, sodium bicarbonate or calcium carbonate.

26. The dressing of claim 22, wherein the gel or gel-forming solution comprises a polyacrylate, a poloxamer, a polyethylene glycol, chitosan, collagen, gelatin, hyaluronic acid, or combinations thereof.

27. The dressing of claim 22, wherein the gel or gel-forming solution comprises a combination of polyacrylate and chitosan.

28. The dressing of claim 22, wherein the gel or gel-forming solution is thermoreversible.

29. The dressing of claim 22, further comprising a non-gas forming porogen.

30. The dressing of claim 29, wherein the non-gas forming porogen is a salt.

31. The dressing of claim 30, wherein the salt is sodium chloride or potassium chloride.

32. The dressing of claim 29, wherein the non-gas forming porogen is a sugar.

33. The dressing of claim 22, wherein the bioresorbable microsphere comprises polylactide (PLA), polyglycolic acid (PLG), poly(lactide-co-glycolide) (PLGA), polyethylene glycol-PLA, PLA-polycaprolactone (PCL), a polyorthoester, a polyphosphazene, or a polyphosphoester.

34. The dressing of claim 22, further comprising a compound that adds stiffness to the dressing.

35. The dressing of claim 34, wherein the compound is calcium sulfate hemihydrate.

36. The dressing of claim 22, further comprising a bioactive agent.

37. The dressing of claim 36, wherein the bioactive agent is an antibiotic.

38. The dressing of claim 36, wherein the bioactive agent is a growth factor.

39. The dressing of claim 38, wherein the growth factor is growth hormone (GH), a bone morphogenetic protein (BMP), transforming growth factor-α(TGF-α), a TGF-β, a fibroblast growth factor (FGF), granulocyte-colony stimulating factor (G-CSF), granulocyte/macrophage colony stimulating factor (GMCSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α(TNF-α), or nerve growth factor (NGF).

40. The dressing of claim 22, further comprising a mammalian cell.

41. The dressing of claim 40, wherein the mammalian cell is an embryonic stem cell, an adult stem cell, an induced pluripotent stem cell, an epithelial cell, an endothelial cell, a mesenchymal cell, a muscle cell, a fibroblast, a chondrocyte, an adipocyte, or an osteocyte.

42. The dressing of claim 40, wherein the mammalian cell is a human cell.

43. The tissue dressing of claim 22, wherein the pores of the scaffold are between approximately 100 micrometers and 300 micrometers in diameter.

* * * * *